United States Patent
Summers et al.

[11] Patent Number: 5,846,756
[45] Date of Patent: Dec. 8, 1998

[54] CHEMILUMINESCENT ANALYTICAL METHOD

[76] Inventors: Malcolm Robert Summers, 63, Chaucer Drive, Aylesbury, Buckinghamshire, HP21 7LH; Graham DeLisle Yearwood, 9, Tewkesbury Court, Warwick Road, Bounds Green, London, N11 2TX; Tracey Michelle Booth, 153, White Hill, Chesham, Buckinghamshire, HP5 1AZ, all of United Kingdom

[21] Appl. No.: 685,399

[22] Filed: Jul. 23, 1996

[51] Int. Cl.$^6$ .................................. C12Q 1/28; C12Q 1/00
[52] U.S. Cl. .................................. 435/28; 435/4; 435/968; 435/975
[58] Field of Search .................................. 435/28, 6, 975, 435/968, 4

[56] References Cited

U.S. PATENT DOCUMENTS

| | | | |
|---|---|---|---|
| 4,598,044 | 7/1986 | Kricka et al. | 435/28 |
| 4,729,950 | 3/1988 | Kricka et al. | 435/28 |
| 4,842,997 | 6/1989 | Carter et al. | 435/28 |
| 5,108,893 | 4/1992 | Baret | 435/28 |
| 5,279,940 | 1/1994 | Kissel | 435/28 |
| 5,340,714 | 8/1994 | Katsilometes | 435/6 |
| 5,512,451 | 4/1996 | Kricka | 435/28 |
| 5,552,298 | 9/1996 | Akhavan-Tafti | 435/28 |

FOREIGN PATENT DOCUMENTS

| | | |
|---|---|---|
| 0569081 | 11/1993 | European Pat. Off. . |
| 62-210988 | 9/1987 | Japan . |

OTHER PUBLICATIONS

Chernyshov, B. N.; Russian Journal of Inorganic Chemistry; 35(9); 1990.

*Primary Examiner*—Louise N. Leary
*Attorney, Agent, or Firm*—Stacey A. Barlow

[57] ABSTRACT

A chemiluminescent analytical method which comprises using a suitable catalyst in a reaction with luminol or a substituted luminol and a perborate in an aqueous solvent and detecting and measuring luminescence produced by the reaction is described. In the method, the aqueous solvent comprises a non-luminescent chelating agent for chelation of an electron-deficient boron atom in the perborate.

10 Claims, 2 Drawing Sheets

Effect of adding glycine to peroxidase / luminol / perborate enhanced chemiluminescent reaction.

| mMole / L glycine | 0 | 0.5 | 1.0 | 2.0 | 4.0 | 5.0 | 15.0 |
|---|---|---|---|---|---|---|---|
| Signal: noise | 14.9 | 17.3 | 21.3 | 23.6 | 38.2 | 32.2 | 37.4 |
| Background | 4.7 | 4.0 | 3.3 | 2.9 | 1.8 | 2.2 | 1.8 |
| 99aMole HRP | 69.5 | 69.0 | 69.3 | 69.0 | 70.0 | 72.2 | 66.6 |

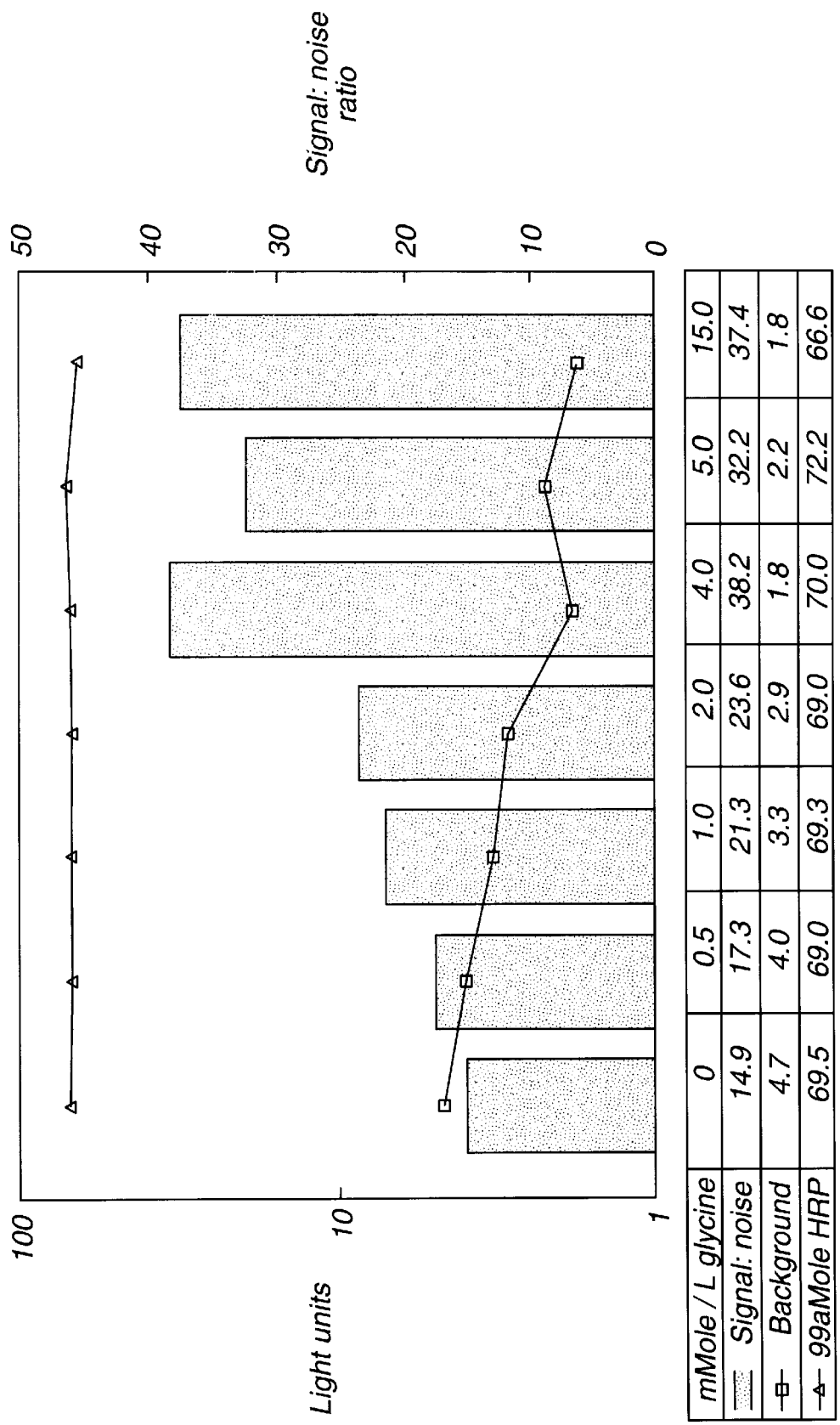

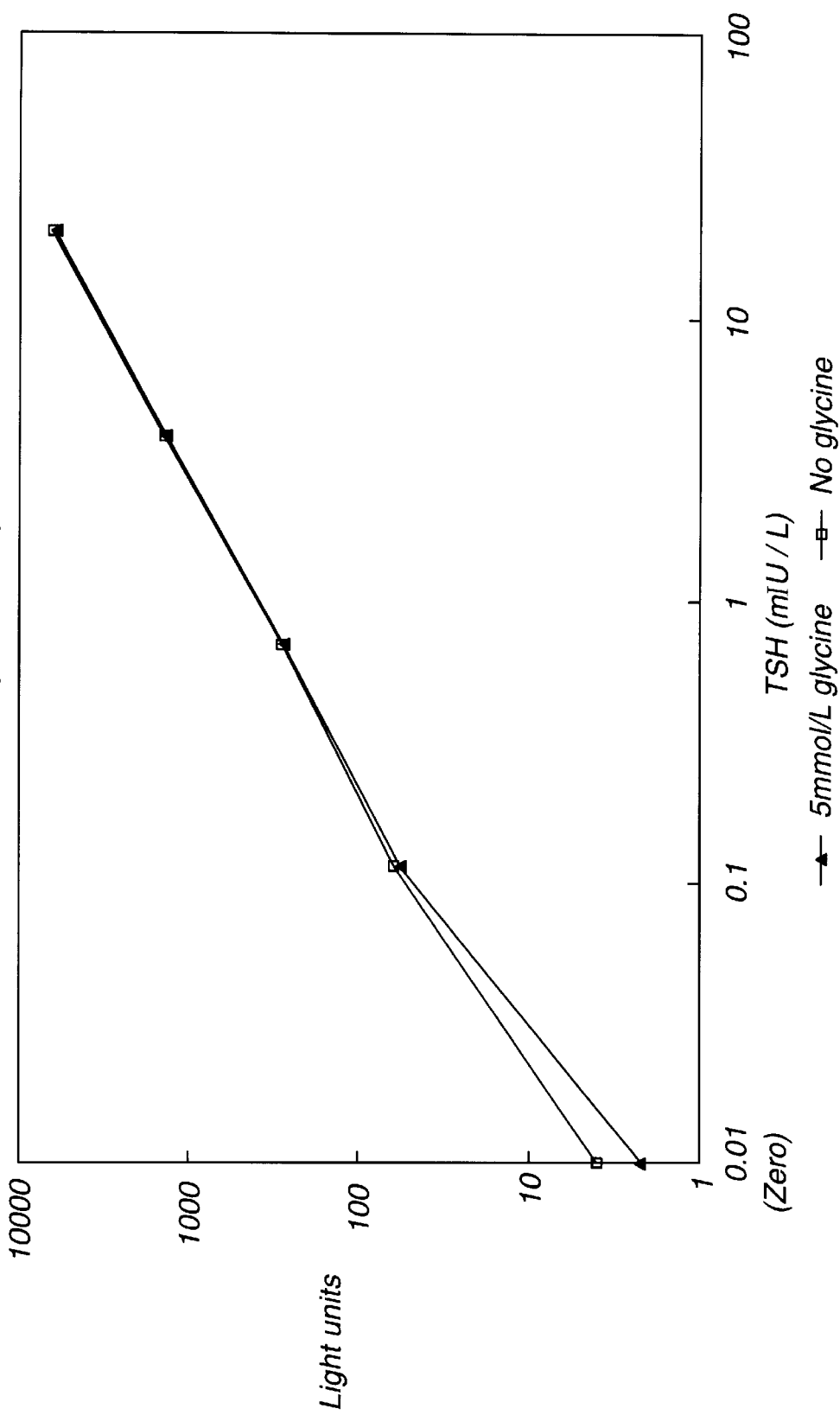

CHEMILUMINESCENT ANALYTICAL METHOD

This invention relates to the field of analytical and diagnostic chemistry for the detection of various analytes in biological fluids. In particular, it relates to a signal-generating composition useful in chemiluminescent assays, to test kits containing same and analytical methods in which the composition and test kits can be used.

Luminescent and luminometric assays are those which produce an emission of light as a result of the presence of an analyte of interest. The light emission is generally of sufficient duration for it to be measured or detected and thereby allow the determination of the analyte.

There are several major types of assays whereby a chemiluminescent signal can be used to advantage to determine an analyte:

1. Assays where a chemiluminescent compound is used to directly label specific binding ligands such as proteins, oligonucleotides, antigens, haptens, hormones, nucleic acids and other compounds of biological interest. Chemiluminescence can be detected by adding a peroxidase and an oxidant to the labelled ligand.

2. Assays where catalysts or cofactors of luminescent reactions are used as labels for specific binding ligands. For example, peroxidase can be conjugated to ligands and used to provide a chemiluminescent signal.

3. Assays where chemiluminescent reactions are used to determine the products formed by action of an enzyme label other than peroxidase on suitable substrates. An example of this type of assay is the determination of a glucose oxidase-labelled specific binding ligand by generating hydrogen peroxidase in the presence of peroxidase.

4. Non-immunoassays to determine a catalyst such as peroxidase or oxidant such as hydrogen peroxide generated as a result of a non-immunoreactant analyte.

Further details of such assays are provided in extensive literature such as U.S. Pat. No. 4,729,950 (Kricka et al) and publications noted therein.

Commonly the source of the hydrogen peroxide involved in the luminescent reaction is a perborate and the substrate for peroxidative action is a 2,3-dihydro-1,4-Phthalazinedione such as luminol. A low level of spontaneous light emission is observed when luminol is mixed with a perborate salt in aqueous solution. Such "background" light emission is undesirable in chemical systems (such as chemiluminescent immunoassays) where light from the controlled oxidation of luminol is measured to determine a reaction endpoint. It is therefore important when designing enzyme immunoassays that such "background" light emission is reduced as much as possible.

According to the present invention we provide a chemiluminescent analytical method which comprises using a suitable catalyst such as a peroxidase enzyme in a reaction with luminol or a substituted luminol and a perborate in an aqueous solvent and detecting and measuring luminescence produced by the reaction characterised in that the aqueous solvent comprises a non-luminescent chelating agent for chelation of an electron-deficient boron atom in the perborate.

Further according to the present invention we provide a reagent useful in a chemiluminescent analytical method which comprises perborate ions in an aqueous solvent characterised in that the aqueous solvent also comprises a non-luminescent chelating agent for chelation of electron-deficient boron atoms in the perborate ions.

Further according to the present invention we provide a kit useful in a chemiluminescent analytical method which comprises a first reagent comprising luminol or a substituted luminol in aqueous solution and a second reagent comprising perborate ions in aqueous solution characterised in that the second reagent also comprises a non-luminescent chelating agent for chelation of electron-deficient boron atoms in the perborate ions.

The first and second reagents of the kit of the present invention may be provided together or separately, in the latter instance being mixed before use or added simultaneously or sequentially to the other compounds of the luminescence reaction. We have demonstrated through analysis of luminol-perborate solutions by fluorescence spectroscopy, that a proportion of the molecules involved co-exist in solution as a complex. A probable mechanism for complex formation is by chelation of the electron-deficient perborate boron atom by luminol. We believe that the complex formed is unstable and that it contributes to background luminescence by decomposing with the emission of light.

We have now found that the background luminescence of luminol-perborate solutions can be reduced by addition of a non-luminescent chelating agent of appropriate molecular geometry, i.e. a non-luminescent chelating agent for chelation of an electron-deficient boron atom in a perborate ion.

We believe that the added chelating agent competes with luminol for perborate binding thereby minimising formation of the unstable luminol-perborate complex.

The mechanism whereby the invention is believed to reduce background luminescence using two preferred chelating agents is shown below in proposed interaction schemes 1 and 2. In scheme 1 the chelating agent is glycine whilst in scheme 2 the chelating agent is sulphosalicylic acid (SSA). In both interaction schemes luminol forms an unstable complex with perborate by loosely binding through oxygen and nitrogen atoms across the electron-deficient boron atom of the perborate ion. In the presence of the chelating agent (glycine in scheme 1 or SSA in scheme 2) an alternative complex forms because the chelating agents have appropriate molecular geometries to replace luminol from the complex. Because of this we believe that background luminescence can be substantially reduced.

1. Proposed Interactions between Perborate, Luminol and Glycine

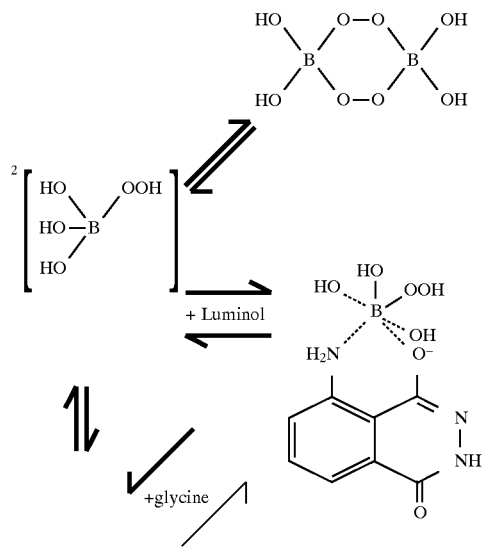

-continued

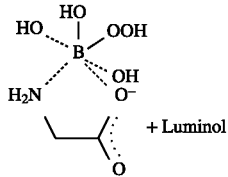
+ Luminol

2. Proposed Interactions between Perborate, Luminol and Sulphosalicyclic acid (SSA)

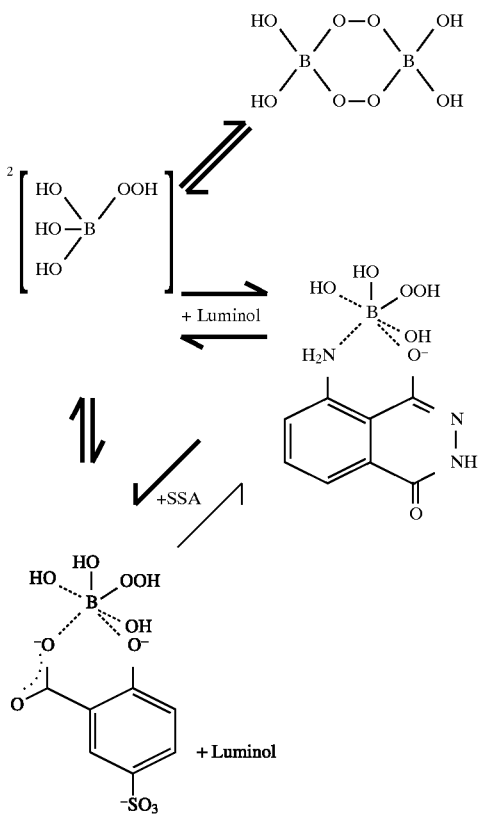

The present invention can be applied to any chemiluminescent analytical method without any particular limitation as long as a suitable catalyst such as a peroxidase enzyme is used and reacted with luminol or a substituted luminol and perborate in an aqueous solvent and the luminescence is then detected and measured. Preferably the catalyst is a peroxidase enzyme which is well known as a labelling substance and has been widely used in assay procedures based on immunological reactions and nucleic acid hybridisation techniques. For example, the peroxidase can be bound to a target by using a target specific binding reagent, the peroxidase bound target is isolated and reacted with luminol and perborate in aqueous solvent. The luminol or substituted luminol and perborate in aqueous solvent are referred to as the signal reagent.

The term "target specific binding reagent" as used herein means a substance which can specifically bond to a target to be analysed. The target may include a physiologically active peptide, a hormone, a nucleic acid and similar substances. When the target to be analysed is capable of acting as an antigen, an antibody (including polyclonal and monoclonal antibodies, antibody fragments and the like) can become a target specific binding reagent. When the target to be analysed is a nucleic acid, its complementary (single strand) nucleic acid or nucleic acid fragment can be a target specific binding reagent.

As chelating agents in the invention may be used any non-luminescent chelating agents having appropriate molecular geometries, i.e. any non-luminescent chelating agents for chelation of an electron-deficient boron atom in a perborate ion. Suitable chelating agents are compounds having a denticity of at least two. Preferred bonding arrangements are bidentate with the chelate ring size of five or six members especially preferred. It is preferred that for the bonding within these systems at least one ligand group carries an electronegative charge. Polydentate or macrocyclic ligands reduce the probability of the perborate becoming detached and so make favoured systems. Preferred chelating agents are glycine and sulphosalicylic acid (SSA) but others may be employed. The concentration of the chelating agent which is suitably present in a typical signal reagent is within the range 4 to 15 mmoles/l but this concentration is dependent to some extent upon the other components of the signal reagent. Suitably the chelating agent is present in stoichiometric excess over both the perborate and the luminol in the signal reagent. In a typical signal reagent the chelating agent will be present in a molar amount between 2 and 10 times the molar amounts of luminol and perborate present therein.

The aqueous solvent used in the analytical method of the invention and present in the signal reagent thereof is generally water or a buffer. Suitable buffers include those buffers usually used in biochemical reactions including in particular phosphate buffer and borate buffer. It may be noted that in the presence of a borate buffer and hydrogen peroxide the complexes mentioned in reaction schemes 1 and 2 can be formed (J Flanagan et al, J.Chem.Soc., Dalton Trans, 1651, 1989: B N Chernyshov, Russian J. Inorg.Chem, 35(9), 1333, 1990). Suitably the buffer has a pH in the range 5 to 12 and preferably in the range 7 to 11. pH values below 5 are outside the optimal pH range for peroxidase enzymes, so that the luminescence emitted becomes lower. pH values above 12 are also outside the optimal range for the enzymes but in this case result in stronger luminescence which does not rely upon the activity of the peroxidase, i.e. give rise to non-specific luminescence.

The preferred catalyst is a peroxidase enzyme but other catalysts may be used including porphyrins such as MP11 (microperoxidase). The peroxidase enzyme used as a labelling substance is suitably a basic isozyme of horseradish (horseradish peroxidase or HRP). Suitable isozymes of horseradish peroxidase include Type VI and Type IX available from Sigma Chemical, Poole, Dorset, Type VI being preferred for use in the invention.

Bonding between the target specific binding reagent and the peroxidase enzyme (i.e. labelling of the binding reagent with the enzyme) may be achieved by any suitable means. The binding reagent and the peroxidase label may be directly bonded together by methods described in M. Brinkley, Bioconj.Chem., 3, page 2, (1992) or similar techniques. Alternatively the target specific binding reagent can be provided with a first chemical group such as a biotinyl group followed by reaction with a peroxidase containing a second chemical group reactive with the first group, such as an avidin or streptavidin residue so that the binding reagent is indirectly labelled.

The luminol for use in the invention is suitably sodium luminol. The perborate used is preferably sodium perborate. It is present as a source of hydrogen peroxide, a substrate for the peroxidase enzyme.

Preferably the signal reagent contains a compound which can enhance the chemiluminescent reaction such as those described in U.S. Pat. No. 4,842,997 and U.S. Pat. No. 5,279,940. In the present invention any enhancer can be used which can facilitate electron transfer from hydrogen peroxide (derived from perborate) via peroxidase to luminol and can exhibit enhancing action. Suitable enhancers include 4-iodophenol, 4-bromophenol, 4-chlorophenol, 4-phenylphenol, 2-chloro-4-phenylphenol, 6-hydroxybenzothiazole, 4-[$4^1$-($2^1$-methyl)thiazolyl]phenol, 4-[$2^1$-($4^1$-methyl)thiazolyl]phenol, 4-($2^1$-benzothiazolyl)phenol, 3-(10-phenothiazyl)-n-propylsulphonate and 3-chloro, 4-hydroxyacetanilide. When the reaction between luminol and hydrogen peroxide is brought about by the peroxidase in the presence of a suitable enhancer, the enhancer increases the rate of oxidation by the enzyme.

In addition to the non-luminescent chelating agent included in the signal reagent to compete with luminol, other chelating agents may also be included to remove unwanted metal ions and for other purposes.

BRIEF DESCRIPTION OF DRAWINGS

The invention is illustrated by the following Examples the results of which are set out graphically in FIGS. 1 and 2 of the accompanying drawings, the drawings being:

FIG. 1: A graph of % of control luminescence, background luminescence and signal-to-noise ratio showing the effect of adding glycine to the peroxidase/luminol/perborate enhanced chemiluminescent reaction in Example 1; and FIG. 2: A graph of light emission in arbitrary light units against thyroid-stimulating hormone (TSH) concentration showing the effect of added glycine on a chemiluminescent TSH immunoassay dose response curve in Example 2.

EXAMPLE 1

Glycine was added to sodium luminol perborate at pH 8.5 in a borate buffer containing citrate and 3-Chloro,4-hydroxy acetanilide (a chemiluminescence enhancer):

Reagent Formula

| Chemical | Concentration (mmole per liter in water) |
|---|---|
| Boric acid | 57.5 |
| Sodium tetraborate | 17.5 |
| Sodium perborate | 2.00 |
| tri-Sodium citrate | 4.65 |
| Citric acid | 2.15 |
| Potassium chloride | 100.0 |
| 3-Chloro,4-hydroxy acetanilide | 0.15 |
| Sodium luminol | 1.00 |
| Glycine | 0 to 15.00 |

As the glycine concentration was increased a reduction of background chemiluminescence was observed. At glycine concentrations above 4 mmole/L, background light output stabilised at about 40% of its initial level. Luminescence catalysed by the addition of about 100 attomoles ($10^{-16}$ mole) of horseradish peroxidase to 250 microliters of the chemiluminescent formation was unaffected by the presence of glycine, the latter producing usefully increased signal-to-noise ratios (see FIG. 1).

Luminescence was measured in white microtiter wells using an "Amerlite" Registered Trade Mark Analyser, Johnson & Johnson Clinical Diagnostics Limited (J&JCDL), Amersham, UK.

EXAMPLE 2

The chemiluminescent formulation in Example 1, containing either zero or 5 mmole per liter glycine, was substituted for the commercial chemiluminescent reagent in the "Amerlite" TSH-30 Ultrasensitive Immunoassay Kit (TSH is human Thyroid-stimulating Hormone) available from J&JCDL, Amersham, UK. The following results were obtained using the published assay protocol:

| | Light signal from zero TSH Standard "A" (20 replicates) | | | Mean Light signal from 0.1130 mIU/L | "B"/ | Assay Sensitivity* |
|---|---|---|---|---|---|---|
| | Mean | s.d. | Coeff. var | TSH Standard "B" | "A" ratio | (mIU/L TSH) |
| No glycine | 4.11 | 0.601 | 14.6% | 62.62 | 15.24 | .0023 |
| 5 mmol/L glycine | 2.34 | 0.351 | 15.0% | 57.77 | 24.69 | .0014 |

*Assay sensitivity is defined as the TSH concentration equivalent to 2 standard deviations (obtained from twenty replicate determinations of the zero standard) above the zero light signal.

With glycine, a lowered zero-standard signal was observed due to a reduction of non-specific background chemiluminescence. There was consequently a higher signal ratio between the first and second assay standards ("B"/"A" ratio). Assuming a linear dose-response characteristic between the two standards, statistical analysis demonstrated that the lower detection limit for TSH (assay sensitivity) improved from 0.0023 to 0.0014 milliInternational Units per Liter with glycine present. This implies a greater capacity of the assay to resolve low levels of TSH—a significant advantage in this type of test.

Other assay performance parameters were unaffected by the addition of glycine (see FIG. 2).

We claim:

1. A chemiluminescent analytical method which comprises using a enzyme catalyst in a reaction with luminol or a substituted luminol and a perborate in an aqueous solvent and detecting and measuring luminescence produced by the reaction characterized in that the aqueous solvent comprises a non-luminescent chelating agent for chelation of an electron-deficient boron atom in the perborate.

2. A method according to claim 1 characterized in that the catalyst is a peroxidase enzyme.

3. A method according to claim 1 or claim 2 characterized in that the non-luminescent chelating agent is a compound having a denticity of at least two.

4. A method according to claim 3 characterized in that the chelate ring size is five or six membered.

5. A method according to claim 4 characterized in that the non-luminescent chelating agent is glycine or sulphosalicylic acid.

6. A method according to any one claim 1 characterized in that the chelating agent is present in a molar amount between 2 and 10 times the molar amounts of luminol or a substituted luminol and perborate present.

7. A reagent which comprises perborate ions in an aqueous solvent characterized in that the aqueous solvent also comprises a non-luminescent chelating agent for chelation of electron-deficient boron atoms in the perborate ions.

8. A reagent according to claim 7 characterized in that the non-luminescent chelating agent is glycine or sulphosalicylic acid.

9. A reagent according to claim 7 or claim 8 characterized in that the non-luminescent chelating agent is present in stoichiometric excess over the perborate in the reagent.

10. A kit useful in a chemiluminescent analytical method which comprises in one or more parts a first reagent comprising luminol or a substituted luminol in aqueous solution and a second reagent comprising perborate ions in aqueous solution characterized in that the second reagent also comprises a non-luminescent chelating agent for chelation of electron-deficient boron atoms in the perborate ions.

* * * * *